US00PP22644P2

(12) United States Plant Patent
Jacobs

(10) Patent No.: US PP22,644 P2
(45) Date of Patent: Apr. 10, 2012

(54) ***LIMONIUM* PLANT NAMED 'ZALIMSAL'**

(50) Latin Name: ***Limonium puberulum*×*Limonium perezii***
Varietal Denomination: Zalimsal

(75) Inventor: Henricus Cornelius Maria Jacobs, Rijsenhout (NL)

(73) Assignee: Van Zanten Plants b.v., Hillegom (NL)

( * ) Notice: Subject to any disclaimer, the term of this patent is extended or adjusted under 35 U.S.C. 154(b) by 0 days.

(21) Appl. No.: 12/931,684

(22) Filed: Feb. 7, 2011

(51) Int. Cl.
*A01H 5/00* (2006.01)

(52) U.S. Cl. ..... Plt./358

(58) Field of Classification Search ..... Plt./358
See application file for complete search history.

*Primary Examiner* — Kent L Bell
(74) *Attorney, Agent, or Firm* — C. A. Whealy

(57) ABSTRACT

A new and distinct cultivar of *Limonium* plant named 'Zalimsal', characterized by its compact, upright and uniformly mounded plant habit; freely flowering habit; violet blue to violet-colored flowers arranged in compact inflorescences; and good garden performance.

1 Drawing Sheet

Botanical designation: *Limonium puberulum*×*Limonium perezii*.

Cultivar denomination: 'ZALIMSAL'.

BACKGROUND OF THE INVENTION

The present invention relates to a new and distinct cultivar of *Limonium* plant, botanically known as *Limonium puberulum*×*Limonium perezii,* commercially used as a potted *Limonium*, and hereinafter referred to by the name 'Zalimsal'.

The new *Limonium* plant is a product of a planned breeding program in Rijsenhout, The Netherlands. The objective of the breeding program is to create new pot-type *Limonium* plants with uniform plant habit and unique flower coloration.

The new *Limonium* plant originated from a cross-pollination conducted by the Inventor in Rijsenhout, The Netherlands in August, 2007 of an unnamed selection of *Limonium puberulum*, not patented, as the female, or seed, parent with a selection of *Limonium perezii* identified as code number 60001-5, not patented, as the male, or seed, parent. The new *Limonium* plant was discovered and selected by the Inventor as a single flowering plant from within the progeny of the stated cross-pollination grown in a controlled environment in Rijsenhout, The Netherlands in May, 2008.

Asexual reproduction of the new *Limonium* plant since July, 2008 by tissue culture in a controlled environment in Rijsenhout, The Netherlands has shown that the unique features of this new *Limonium* plant are stable and reproduced true to type in successive generations.

SUMMARY OF THE INVENTION

Plants of the new *Limonium* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Zalimsal'. These characteristics in combination distinguish 'Zalimsal' as a new and distinct *Limonium* plant:

1. Compact, upright and uniformly mounded plant habit.
2. Freely flowering habit.

3. Violet blue to violet-colored flowers arranged in compact inflorescences.
4. Good garden performance.

Plants of the new *Limonium* can be compared to plants of the female parent selection. Plants of the new *Limonium* differ primarily from plants of the female parent selection in plant size as plants of the new *Limonium* are taller than plants of the female parent selection. In addition, plants of the new *Limonium* have larger flowers than plants of the female parent selection.

Plants of the new *Limonium* can be compared to plants of the male parent selection. Plants of the new *Limonium* differ primarily from plants of the male parent selection in plant size as plants of the new *Limonium* are more compact than plants of the male parent selection.

Plants of the new *Limonium* can be compared to plants of *Limonium perezii* 'F.T. Hubbard', not patented. In side-by-side comparisons conducted in Rijsenhout, The Netherlands, plants of the new *Limonium* differed primarily from plants of 'F.T. Hubbard' in the following characteristics:

1. Plants of the new *Limonium* were more compact than plants of 'F.T. Hubbard'.
2. Inflorescences of plants of the new *Limonium* were more compact than and not as open as inflorescences of plants of 'F.T. Hubbard'.
3. Plants of the new *Limonium* had smaller flowers than plants of 'F.T. Hubbard'.
4. Plants of the new *Limonium* had a shorter flowering cycle than plants of 'F.T. Hubbard'.

BRIEF DESCRIPTION OF THE PHOTOGRAPH

The accompanying colored photograph illustrates the overall appearance of the new *Limonium* plant showing the colors as true as it is reasonably possible to obtain in colored reproductions of this type. Colors in the photograph may differ slightly from the color values cited in the detailed botanical description which accurately describe the colors of the new *Limonium* plant. The photograph comprises a side perspective view of a typical flowering plant of 'Zalimsal' grown in a container.

DETAILED BOTANICAL DESCRIPTION

The aforementioned photograph and following observations and measurements describe plants of the new *Limonium* grown during the summer in 19-cm containers in a glass-covered greenhouse in Rijsenhout, The Netherlands and under potted *Limonium* production conditions. During the production of the plants, day temperatures ranged from 18° C. to 25° C. and night temperatures ranged from 16° C. to 18° C. Plants were 16 weeks old when the photograph and description were taken. Color references are made to The Royal Horticultural Society Colour Chart, 1991 Edition, except where general terms of ordinary dictionary significance are used.

Botanical classification: 'Limonium puberulum×Limonium perezii Zalimsal'.

Parentage:

*Female, or seed, parent.*—Unnamed selection of *Limonium puberulum*, not patented.

*Male, or pollen, parent.*—Selection of *Limonium perezii* identified as code number 60001-5, not patented.

Propagation:

*Type.*—By tissue culture.

*Time to initiate roots, summer.*—About 35 days at temperatures of 20° C.

*Time to initiate roots, winter.*—About 35 to 40 days at temperatures of 18° C. to 25° C.

*Root description.*—Fine, fibrous; white in color.

*Rooting habit.*—Moderate branching; medium density.

Plant description:

*Plant and growth habit.*—Perennial subshrub grown as a potted and landscape plant; plants compact, upright and uniformly mounded; broad inverted triangular plant form; leaves basal; freely branching habit; freely flowering habit; numerous flowers arranged in compact panicles; moderately vigorous growth habit.

*Plant height.*—About 25 cm to 35 cm.

*Plant diameter* (*spread*).—About 25 cm to 30 cm.

*Flowering stems.*—Length: About 25 cm to 35 cm. Diameter: About 5 mm to 8 mm. Internode length: About 2 cm to 10 cm. Aspect: About 20 to 30° from vertical. Strength: Strong. Texture: Smooth, glabrous. Color: Close to 146A.

Foliage description:

*Arrangement.*—Basal rosette, simple.

*Length.*—About 8 cm to 10 cm.

*Width.*—About 3 cm to 6 cm.

*Shape.*—Obovate.

*Apex.*—Obtuse.

*Base.*—Attenuate.

*Margin.*—Entire; slightly undulate.

*Texture, upper and lower surfaces.*—Pubescent.

*Venation pattern.*—Pinnate.

*Color.*—Developing leaves, upper surface: Close to 147A tinged with close to 183A. Developing leaves, lower surface: Close to 183A. Fully expanded leaves, upper surface: Close to 137B to 137C; venation, close to 137C. Fully expanded leaves, lower surface: Close to 147B; venation, close to 139D.

*Petioles.*—Length: About 3 cm to 7 cm. Diameter: About 2 mm to 3 mm. Texture, upper and lower surfaces: Pubescent. Color, upper and lower surfaces: Close to 138A to 138B.

Flower description:

*Flower arrangement and habit.*—Single flowers arranged in compact panicles; freely flowering habit with about 300 flowers developing per inflorescence; flowers actinomorphic and symmetrical; flowers face mostly upright.

*Fragrance.*—Absent or faint, aromatic.

*Flowering response.*—In The Netherlands, plants begin flowering about 20 weeks after planting; plants flower year round in the greenhouse.

*Post-production longevity.*—Flowers last for about 25 days; corolla not persistent, calyx persistent.

*Inflorescence height.*—About 10 cm to 25 cm.

*Inflorescence diameter.*—About 10 cm by 15 cm.

*Flower diameter.*—About 5 mm to 6 mm.

*Flower depth* (*height*).—About 5 mm to 8 mm.

*Flower buds.*—Length: About 5 mm to 8 mm. Diameter: About 1 mm to 2 mm. Shape: Ellipsoidal. Color: Towards the apex, close to 93B; towards the base, close to 147C.

*Corolla.*—Petals per flower: Five in a single whorl, fused. Petal length: About 5 mm to 8 mm. Petal width: About 3 mm to 5 mm. Petal shape: Fusiform, roughly deltoid. Petal apex: Acute: Petal margin: Entire. Petal texture, upper and lower surfaces: Smooth, glabrous; satiny. Petal color: When opening, upper and lower surfaces: Close to 155A. Fully opened, upper and lower surfaces: Close to 155A.

*Calyx.*—Sepals per flower: Five in a single whorl, fused; calyx cup-shaped. Sepal length: About 5 mm to 6 mm. Sepal diameter: About 3 mm to 5 mm. Sepal shape: Deltoid. Sepal apex: Acute. Sepal base: Fused. Sepal margin: Entire. Sepal texture, upper and lower surfaces: Smooth, glabrous; papery. Sepal color: When opening and fully opened, upper surface: Close to 93B and 86C. When opening and fully opened, lower surface: Close to 93B and 86C.

*Peduncles.*—Length: About 1 cm to 10 cm. Diameter: About 1 mm to 4 mm. Strength: Strong. Angle: About 20 to 40° from stem axis. Texture: Slightly pubescent. Color: Close to 137B to 137C.

*Pedicels.*—Length: About 1 mm to 5 mm. Diameter: About 1 mm. Strength: Strong. Angle: About 20 to 40° from peduncle axis. Texture: Slightly pubescent. Color: Close to 137B and 139C.

*Reproductive organs.*—Androecium: Stamen number: Five per flower. Filament length: About 2 mm to 4 mm. Filament color: Close to 155A. Anther length: About 0.8 mm to 1.2 mm. Anther shape: Elliptical. Anther color: Close to 155D. Amount of pollen: Abundant. Pollen color: Close to 11D. Gynoecium: Pistil number: Five per flower. Pistil length: About 2 mm to 3 mm. Style length: About 1 mm to 2 mm. Style color: Close to 155D. Stigma shape: Capitate, filiform. Stigma color: Close to 155D.

*Seeds and fruits.*—Seed and fruit development have not been observed on plants of the new *Limonium*.

Disease/pest resistance: Plants of the new *Limonium* have not been observed to be resistant to pathogens and pests common to *Limonium*.

Garden performance: Plants of the new *Limonium* have been observed to have good garden performance and to tolerate wind, rain and temperatures ranged from about 5° C. to about 35° C.

It is claimed:

1. A new and distinct *Limonium* plant named 'Zalimsal' as illustrated and described.

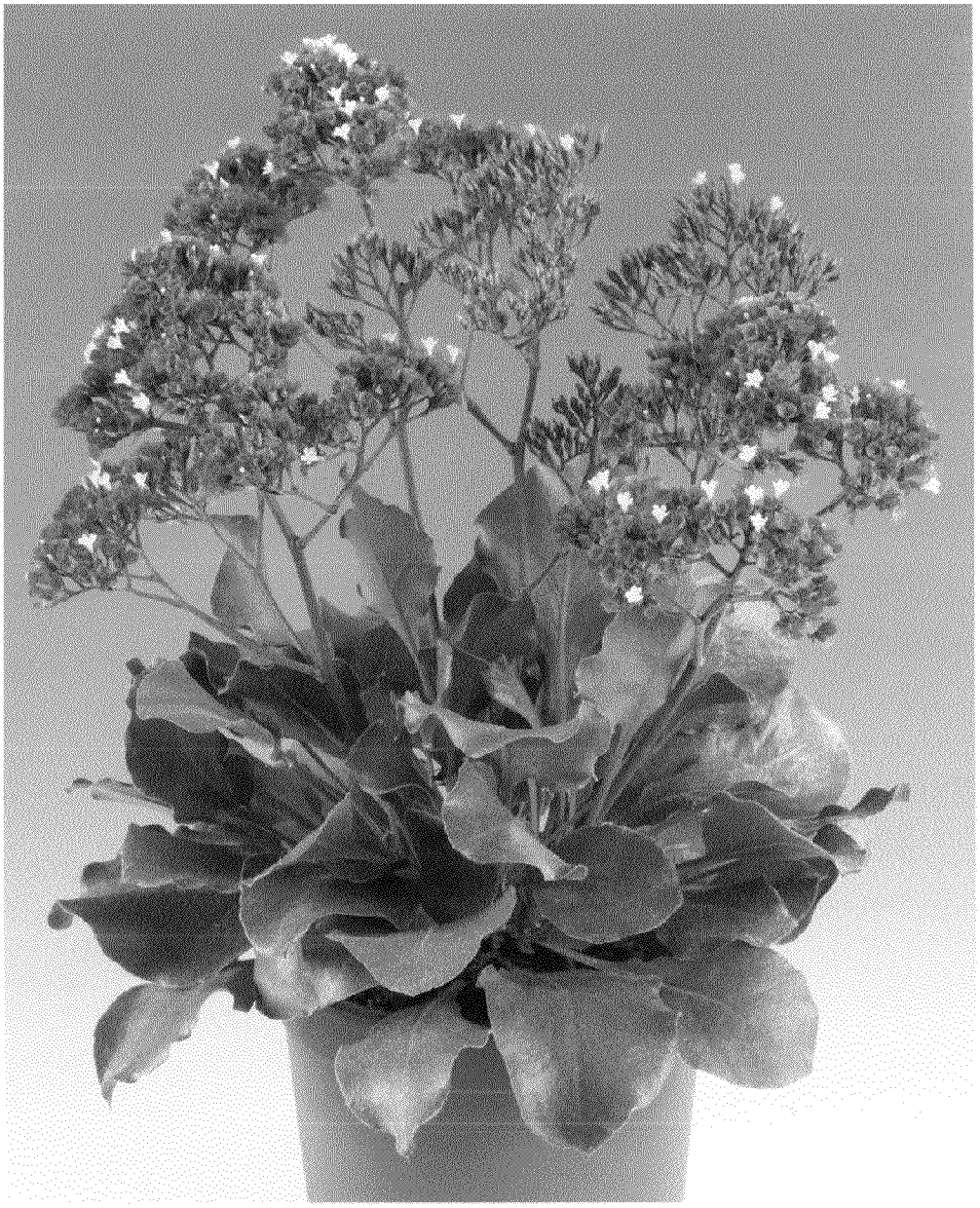

* * * * *